(12) United States Patent
Sadygov

(10) Patent No.: US 7,680,606 B2
(45) Date of Patent: Mar. 16, 2010

(54) TWO-STEP METHOD TO ALIGN THREE DIMENSIONAL LC-MS CHROMATOGRAPHIC SURFACES

(75) Inventor: Rovshan Goumbatoglu Sadygov, San Jose, CA (US)

(73) Assignee: Thermo Finnigan LLC, San Jose, CA (US)

( * ) Notice: Subject to any disclaimer, the term of this patent is extended or adjusted under 35 U.S.C. 154(b) by 176 days.

(21) Appl. No.: 11/703,942

(22) Filed: Feb. 7, 2007

(65) Prior Publication Data

US 2008/0046447 A1   Feb. 21, 2008

Related U.S. Application Data

(60) Provisional application No. 60/771,601, filed on Feb. 8, 2006.

(51) Int. Cl.
*G01N 33/48* (2006.01)
(52) U.S. Cl. ........................................................ 702/19
(58) Field of Classification Search ................ 702/19
See application file for complete search history.

(56) References Cited

U.S. PATENT DOCUMENTS

| | | | |
|---|---|---|---|
| 6,906,320 | B2 | 6/2005 | Sachs et al. |
| 6,989,100 | B2 | 1/2006 | Norton |
| 2005/0065732 | A1 | 3/2005 | Tilton et al. |
| 2005/0170372 | A1 | 8/2005 | Afeyan et al. |
| 2005/0288872 | A1 | 12/2005 | Old et al. |
| 2006/0020401 | A1 | 1/2006 | Davis et al. |
| 2006/0131222 | A1 | 6/2006 | Norton |

OTHER PUBLICATIONS

Prince et al., "Chromatographic Alignment of ESI-LC-MS Proteomics Data Sets by Ordered Bijective Interpolated Warping," Anal. Chem., vol. 78 ( No. 17), p. 6140-6152, (2006).
Prince et al., "Chromatographic Alignment of Multi-Dimensional Mass Spectra Using Interpolated Dynamic Time Warping," 53rd ASMS Conference, San Antonio, TX., 2 pgs, (2005).
Dharsee et al., "Automated Quantitation and Comparative Proteomic Analysis of Complex Biological Samples," 53rd ASMS Conference, San Antonio, TX, 2 pgs., (2005).
Sadygov et al., "ChromAlign: A Two-Step Algorithmic Procedure for Time Alignment of Three-Dimensional LC-MS Chromatographic Surfaces," Anal. Chem, vol. 78, p. 8207-8217, (2006).

*Primary Examiner*—Jerry Lin
(74) *Attorney, Agent, or Firm*—Charles B. Katz

(57) ABSTRACT

A two-step alignment method for temporally aligning LC-MS data files representative of three-dimensional chromatographic surfaces is disclosed. The method includes a pre-alignment step whereby the data files are roughly aligned using a transformation-based correlation analysis of base peak information. The pre-aligned files are used as input to a full alignment step, in which a correlation matrix is computed from the full MS scan information, and an optimal path is traced through the resultant correlation matrix to identify corresponding scan numbers. The use of the pre-alignment step substantially reduces the computational expense of the full alignment step and improves the accuracy and reliability of the alignment.

11 Claims, 5 Drawing Sheets

TWO-STEP METHOD TO ALIGN THREE DIMENSIONAL LC-MS CHROMATOGRAPHIC SURFACES

CROSS-REFERENCE TO RELATED APPLICATION

This application claims the priority benefit under 35 U.S.C. §119(e) of U.S. provisional application No. 60/771,601 entitled "A Two-Step Method to Align Three Dimensional LC-MS Chromatographic Surfaces" filed on Feb. 8, 2006, the disclosure of which is incorporated herein by reference.

BACKGROUND OF THE INVENTION

1. Field of the Invention

The present invention relates generally to analysis of LC-MS data, and more particularly to methods for temporal alignment of data files representative of chromatographic surfaces.

2. Description of the Related Art

Mass spectrometry has become a key analytical tool for studies in the field of proteomics. In such studies, different samples containing collections of proteins are separately analyzed in a mass spectrometer, and the resultant mass spectral data are compared in order to, for example, identify differential expression of one or more proteins that may be indicative of a disease state. Because the samples often contain complex mixtures comprising numerous component species, liquid chromatography is often employed to provide temporal separation of the different species and thereby simplify the interpretation of the mass spectral data. A problem associated with the use of LC-MS for proteomics studies arises from the inherent variability of chromatographic separation. Due to column aging and changes in experimental conditions, the time after injection at which a known species elutes from the column and is introduced into the mass spectrometer is not constant, but instead will vary from one chromatographic run to the next. Furthermore, the shift in elution times is not static, but instead changes from one species to another. This phenomenon is often referred to in the art as "time warping", and must be accounted for and corrected when performing comparisons of mass spectral data.

A number of approaches are disclosed in the prior art for identifying and correcting chromatographic time warping (hereinafter referred to as alignment techniques). Earlier alignment techniques have focused on alignment of HPLC and gas phase chromatographic profiles where elution dynamics of only base peaks (the major features of the chromatogram) are considered. These techniques disregard other peaks of full mass scans. Methods that have been developed for alignment of chromatographic profiles include dynamic time warping (DTW), correlation-optimized warping (COW), parametric time warping, and parallel factor analysis. A salient characteristic of these methods is that they are designed to align two-dimensional chromatographic profiles, in which one dimension is time and the other is the measured base peak intensity; such methods do not comprehensively use mass informatics information (the mass-to-charge or m/z values of the detected ions) for the alignment calculation. The primary drawback of techniques of this general description is that they tend to align the most intense peaks in the chromatograms without regard to the mass origin of the peaks, which may lead to erroneous results.

More recently, chromatographic alignment techniques have been developed which comprehensively utilize mass informatics information to produce more reliable and accurate alignment of data files One such technique (see J. T. Prince and E. M. Marcotte, *Chromatographic Alignment of Multi-Dimensional Mass Spectra using Interpolated Dynamics Time Warping*, 53$^{rd}$ ASMS Conference, San Antonio, Tex., 2005) involves the use of correlation or dot product analysis between full MS scans to generate a correlation matrix and identify an optimal path. It has been found, however, that this technique works well only where the chromatographic time shifts are relatively small. For large chromatographic shifts, this technique may involve excessive computational expense and/or may result in paths that provide inaccurate alignment.

SUMMARY

Roughly described, an embodiment of the present invention provides a method for temporally aligning data files representative of three-dimensional LC-MS surfaces, the method having two steps: an initial step in which the data files are pre-aligned using base peak information only, and a subsequent alignment step in which a correlation matrix is constructed from full MS scan data in the pre-aligned data files and an optimal path through the correlation matrix is determined. The pre-alignment step may involve constructing two-dimensional chromatographic profiles using base peak retention times and intensities and determining a time shift that maximizes the dot product of the two-dimensional chromatographic profiles. The time shift may be calculated, for example, by a transformation-based (e.g., using the Fourier transform) correlation analysis. The calculated time shift is then utilized to produce pre-aligned data files, which are used as input to the subsequent alignment step.

The correlation matrix is populated by calculating the Pearson correlation coefficients for pairs of MS scans from the pre-aligned data files. To reduce computational expense, the correlation coefficients are calculated only for those scan pairs that fall within a time window around the time shift determined in the pre-alignment step. The optimal path through the correlation matrix may utilize a dynamic programming technique, in which a path matrix is constructed whose every element corresponds to the optimal path thereto, and a path is traced from the end point to the starting point.

By employing the pre-alignment step prior to constructing the correlation matrix, accurate alignment of data files may be achieved without incurring unacceptable computational expense, thereby avoiding problems associated with prior art solutions.

DESCRIPTION

Figure 1:
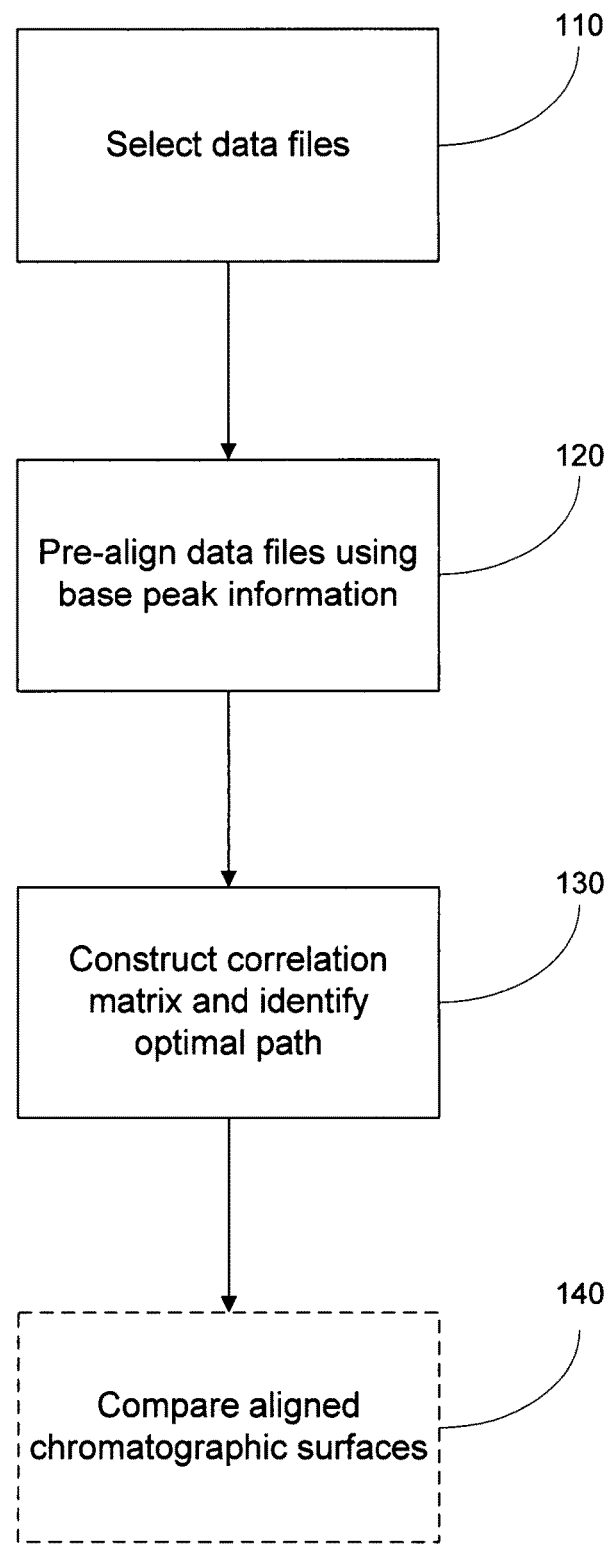
FIG. 1 is a flowchart depicting the steps of a method for temporally aligning data files representative of three-dimensional LC-MS surfaces, in accordance with an exemplary embodiment of the invention.

An embodiment of a temporal alignment method of the present invention may be better understood with reference to the FIG. 1 flowchart. The method described herein will typically be implemented as a set of software instructions (e.g., in a C++ program) that is executable on a general-purpose processor. The method accepts as input a plurality of data files, each data file containing mass spectrometric data acquired during a different chromatographic run. Typically, a proteomics or similar study will produce a relatively large number of data files which need to be temporally aligned to each other in order to identify variations in the presence or quantity of a protein or peptide of interest. This may be done by designating one of the data files as the reference data file, and then aligning each of the remaining data files (which will be referred to as sample data files) to the reference data file. Data files generated by commercial mass spectrometers are commonly formatted as RAW files, which contain the measured (m/z, time, intensity) data points for each analytical scan (MS or MS") performed during analysis of a sample. The data may be generated using a mass spectrometer having any suitable mass analyzer or combination of mass analyzers, including (without limitation) a quadrupole ion trap, electrostatic trap or FTICR analyzer. Scans are performed sequentially during a chromatographic run, and each scan is assigned a scan number that can be uniquely mapped to a chromatographic time. The data files can thus be considered to represent three dimensional LC-MS chromatographic surfaces, in which the three orthogonal dimensions are time, m/z and intensity. In the embodiment described herein, data for MS scans is used for temporal alignment. The MS" scan data can also be used for alignment in the cases where specific species rather than whole chromatographic surfaces are aligned.

In step 110, two data files are selected for alignment. As noted above, one data file may be designated as the reference data file and the other as the sample data file; however, application of the alignment method described herein will yield identical results irrespective of which data file is designated as the reference data file. Optionally, the data files may be preprocessed using well-known filters or algorithms prior to application of the alignment steps. Examples of preprocessing techniques include (without limitation) baseline subtraction, thresholding, smoothing, noise reduction, normalization, and peak detection. The data points may also be aggregated into bins falling within a specified m/z or time interval (e.g., time bins of 0.1 second duration).

Next, in step 120, the sample data file is pre-aligned to the reference data file using only the base peak information (representative of the most intense peak in each mass spectrum) present in the data files. The pre-alignment step involves constructing two-dimensional chromatographic profiles using base peak retention times and intensities from the reference and sample data files and determining a time shift that maximizes the dot product of the chromatographic profiles. In one implementation, the time shift may be determined from correlation analysis between the chromatographic profiles using Fourier transforms. As is well-known, a correlation of arrays can be computed as an inverse Fourier transform of the product of their individual Fourier transforms, $$\text{Corr}(A,B) = F^{-1}(F(B)F(A)^*)$$

where F(B) is the Fourier transform of the chromatographic profile derived from data file B (e.g., the sample data file), F(A)* is the complex conjugate of the Fourier transform of the chromatographic profile derived from data file A (e.g., the reference data file), and $F^{-1}$ is the inverse Fourier transform. Since the data files contain discrete data, the Fourier transform is given by (for example, for the chromatographic profile derived from data file A):

$$F(A)_n = \sum_{k=0}^{N-1} A_k e^{2\pi i n k / N}$$

where $A_k$ is the intensity of the kth base peak, and N is the number of base peaks in the data file. Thus, for every alignment of the two chromatographic profiles, several Fourier transforms are performed. In a typical software implementation, Fast Fourier Transforms (FFTs) are employed to compute the discrete Fourier transform and its inverse. Application of the FFT analysis yields a correlation array representing, for different time (scan number) shifts, the degree of correlation between the major features of the chromatographic profiles derived from the test and sample data files. The time shift that maximizes the correlation between the chromatographic profiles is selected and applied to one of the data files (e.g., by shifting scan numbers of the sample data file B) to pre-align the data files. The correlation array may also be used to determine a time window, centered on the time shift, outside of which the scans (or more particularly, the base peak information derived therefrom) are poorly correlated. As will be discussed below, computation of a time window in the pre-alignment step 120 substantially reduces the computational expense of the subsequent alignment step 130 by avoiding the need to compute the entire correlation matrix; instead, correlation values for only those elements that fall within the time window are computed.

It will be appreciated that pre-alignment of the data files (which requires relatively few computational cycles and thus may be completed quickly) prior to construction of the correlation matrix offers several important advantages over prior art techniques, including eliminating the need to calculate a computationally expensive full correlation matrix, reducing identification of false paths leading to inaccurate alignment, and avoiding introduction of any parameter files, e.g., a user-specified slack parameter, which are prone to misuse and misinterpretation. Those skilled in the art will recognize that other forms of transformations (e.g., the Laplace transformation) can be used in place of the FFT analysis outlined above for the pre-alignment step.

Following completion of the pre-alignment step 120, a detailed alignment of the pre-aligned data files A and B' is performed, step 130 (for the purpose of providing an example, we will assume that A is the reference data file and that B' is the time-shifted sample data file.) For the detailed alignment step, a correlation matrix between the full MS scan data of the two data files is generated. The correlation matrix is populated by the Pearson coefficients calculated from the full MS data. To convert the fill mass scans into arrays used in the Pearson correlation, m/z data may be aggregated into bins at integer values. Assuming that data files A and B' respectively contain N and M full mass scans, the correlation matrix C is a two-dimensional matrix with M rows and N columns. The element of C is the Pearson correlation of the $i^{th}$ full scan of data file A, $X_i$, and the $j^{th}$ full scan of the pre-aligned data file B', $Y_j$, and is calculated according to the equation:

$$c_{ij} = \frac{\sum_{\alpha=1}^{K}(X_\alpha^i - \overline{X})(Y_\alpha^j - \overline{Y})}{K \sigma_A^i \sigma_{B'}^j}$$

where $X_\alpha^i$ and $X_\alpha^j$ are the intensities of $\alpha^{th}$ (m/z binned) peaks in the $i^{th}$ fill mass scan of A and $j^{th}$ full mass scan of B', respectively, K is the number of mass peaks (integer value of the highest mass peak) in the scans, and $\sigma_A^i$ and $\sigma_B^j$ are the standard deviations of the $i^{th}$ and $j^{th}$ full mass scans of A and B', respectively.

In a preferred implementation of the alignment method, Pearson correlations are calculated only for those elements $c_{ij}$ that fall inside a band of correlation matrix C having a width corresponding to the time window (alternately and equivalently expressed as a scan number window) determined in pre-alignment step 120. Limiting calculation of Pearson correlations to these elements substantially reduces the overall computation time required for alignment, and avoids the identification of false (inaccurate) paths in the subsequent path optimization process.

After the matrix has been populated with the Pearson correlations, an optimal path through the correlation matrix C is established. This is done by selecting a combination of pairwise scan alignments that maximizes the sum of the correlations. In one implementation, only a single boundary condition is applied, namely that the first MS scans of the two data files are aligned. The alignments that are selected must meet certain path criteria and connection rules (e.g., "looping" paths are avoided) such that the resultant optimized path does not represent a false (i.e., physically impossible or highly improbable) temporal alignment solution.

In general, the computational solution of the optimized path problem grows exponentially with the size of the correlation matrix. However, the computational time required to identify the optimal path may be drastically reduced by employing well-known dynamic programming techniques. In a dynamic programming-based implementation, a matrix D is constructed, whose every element corresponds to an optimal path leading to the specific element. The elements D(i,j) are determined from the following relation:

$$D(i, j) = \max \{D(l, k) + c(i, j)\}$$

where l changes between $i-i_0$ and i, and k changes between $j-j_0$ and j. The values of $i_0$ and $j_0$ are determined in pre-alignment step 120 and correspond to the determined time shift and time window. The boundary condition (alignment of the first scans of the two data files) requires that:

$$D(1,1) = c(1,1)$$

After the path matrix D is populated, the optimal path through the correlation matrix is identified by starting with the alignment of the end points and determining the previous point that led to it, and then repeating this procedure until the starting point is reached. The recorded path is the optimal path that is used to identify corresponding scans from the sample and reference data files for temporal alignment thereof. An alignment score, based on the sum of Pearson correlations along the optimal path, may be calculated and provided to a user. This score is representative of the quality of the alignment between the data files.

The computational time required for completing alignment step 130 may be reduced by employing various tools available in the art. In one specific example, single-instruction, multiple data (SEID) technology is employed to provide accelerated execution of the alignment algorithm. This technology is based on the MultiMedia extensions and streaming SIMD extensions (SSE) technologies embedded in many commercially-available microprocessors. In a study conducted by the applicant on a dataset consisting of nine data files generated by analysis of a nine-protein mixture sample (Sadygov et al., Anal. Chem. 2006, 78 8207-8217), it was found that the use of SSE technology reduces the time required to complete alignment by 23% relative to a conventional (no pre-alignment, no SSE) alignment method. When combined with the pre-alignment step described above, a 57% time savings is realized relative to the conventional alignment method.

When multiple sample data files within a data set are to be temporally aligned, steps 110-130 may be repeated for each data file to align the selected data file with the reference data file. After all data files have been aligned, the aligned data files may be compared to identify features that differentiate the LC-MS chromatographic surfaces represented by the data files, step 140. For example, a peak that occurs in only certain spectra (or appears at a markedly different intensity) may indicate a biological marker associated with a characteristic of the relevant samples, such as the presence or absence of a diseased state. The comparison may be performed by simply displaying the aligned chromatographic surfaces (or profiles derived therefrom) to the user, or may alternatively utilize an automated technique by which differences between and among the chromatographic surfaces are identified and highlighted.

Figure 2A:
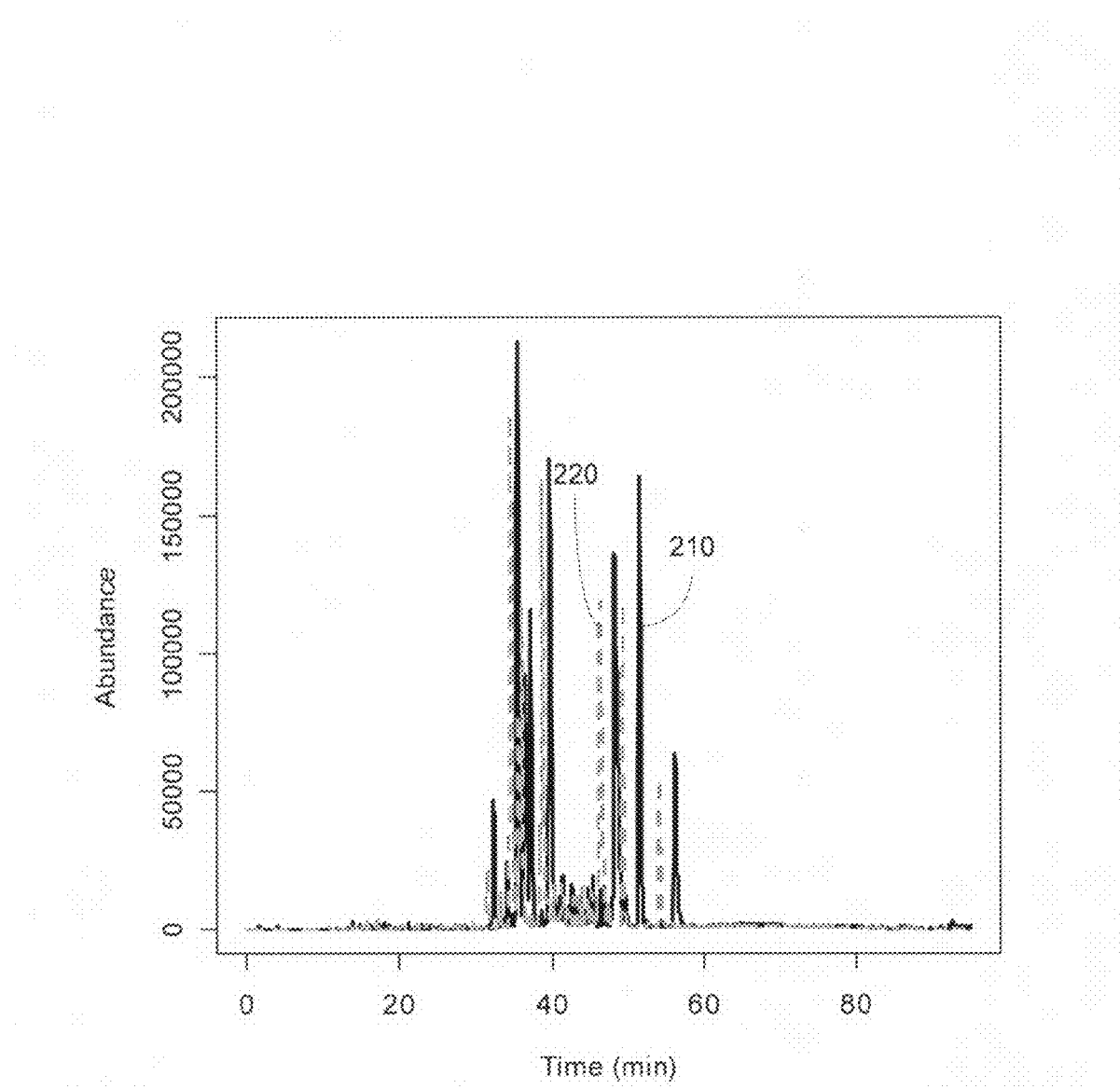
FIG. 2A depicts an example of reference and sample chromatograms before alignment.
Figure 2B:
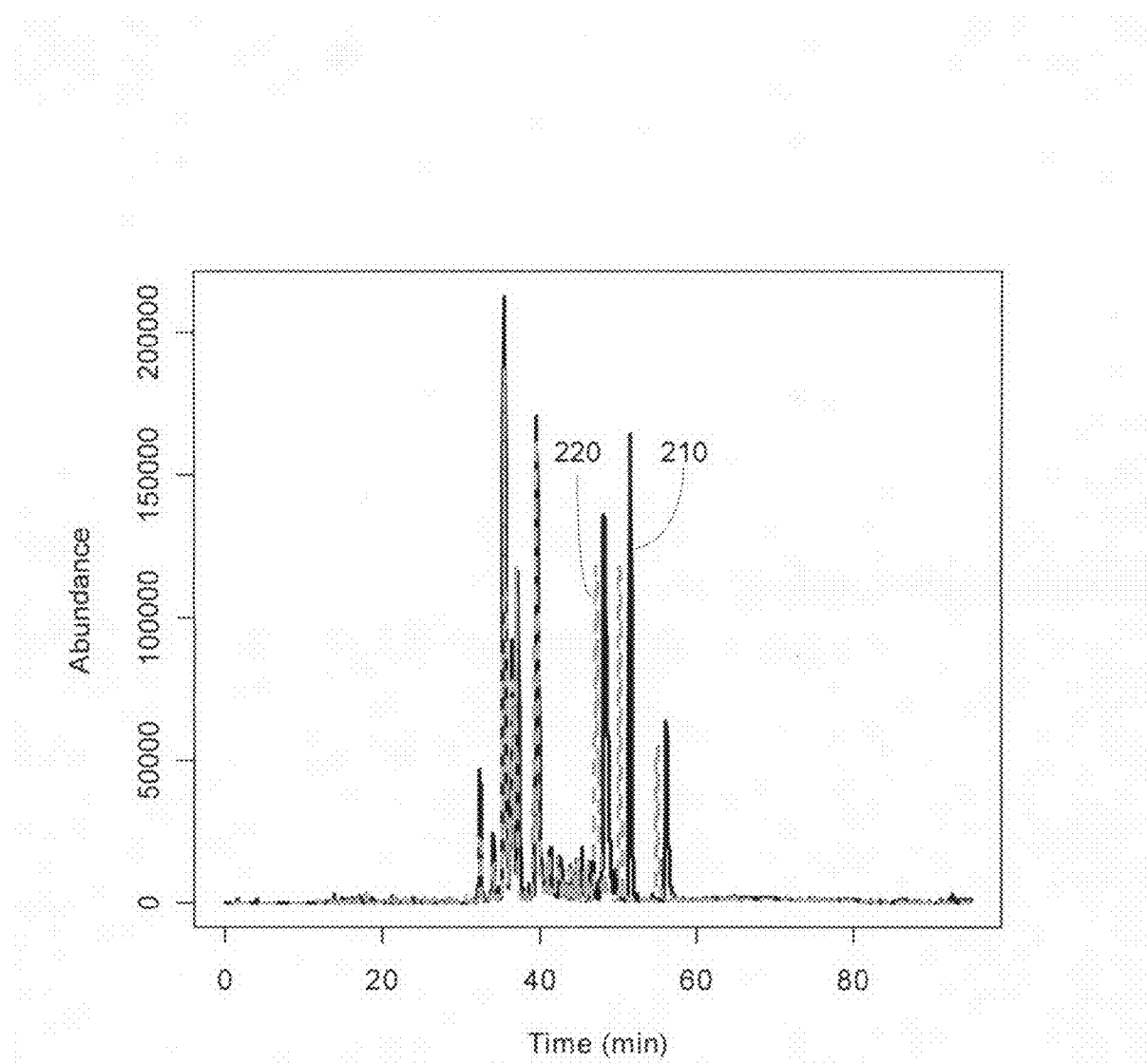
FIG. 2B depicts partially aligned reference and sample chromatograms after the pre-alignment step.
Figure 2C:
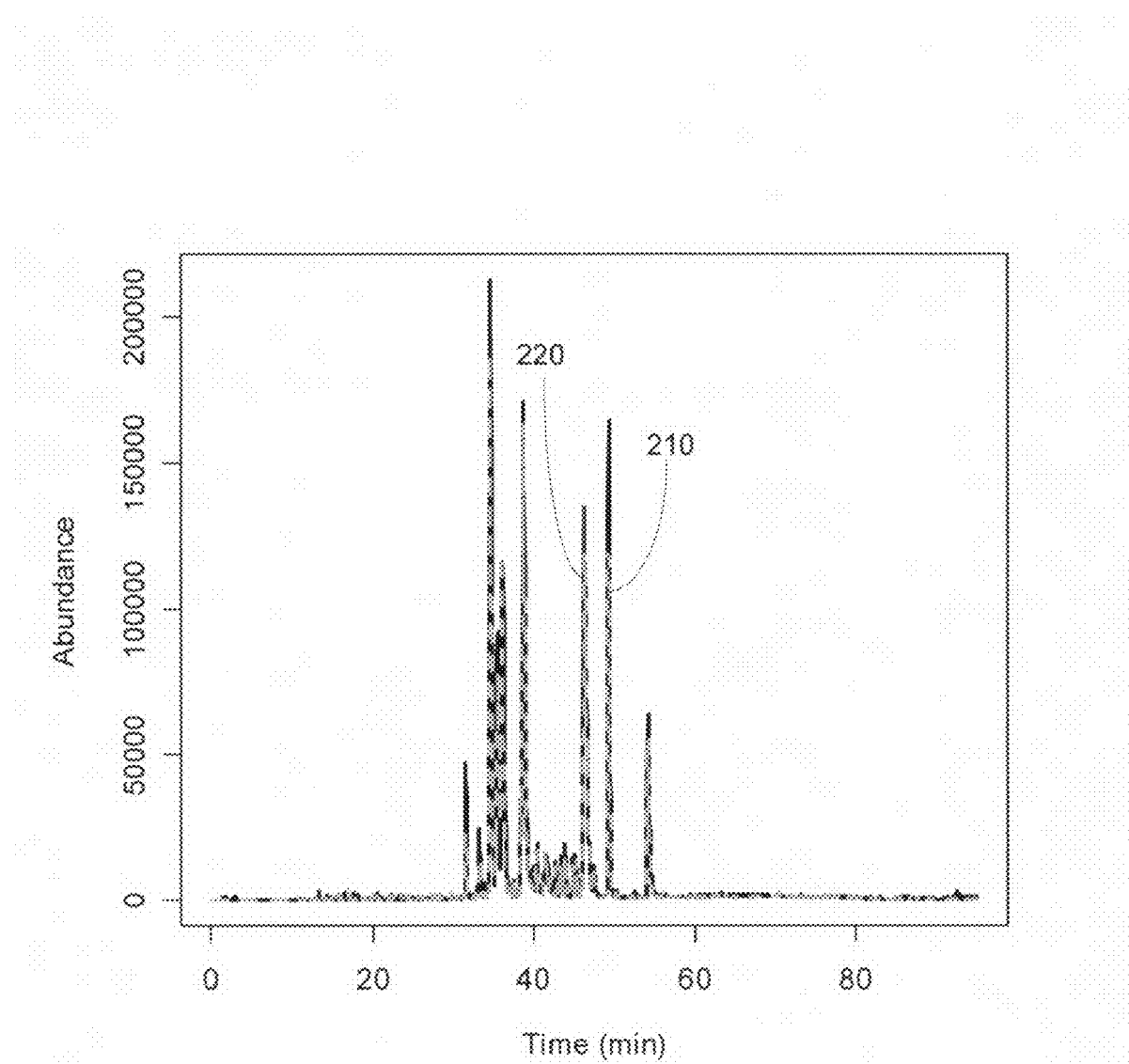
FIG. 2C depicts the aligned reference and sample chromatograms following application of the second alignment step.

FIGS. 2A-2C illustrate results obtained using the alignment method described above. FIG. 2A depicts two chromatographic profiles derived from unaligned data files obtained by LC-MS analysis of a nine-protein mixture digest. The first chromatographic profile 210 is drawn in black and is referred to as the reference profile, and the second chromatographic profile 220 is draw in gray and is referred to as the sample profile. It is noted that while the method described and claimed herein provides for alignment of three-dimensional surfaces rather than two-dimensional profiles, only the profiles are shown in the figures due to the practical complications associated with depicting complex surfaces. The profiles shown in FIGS. 2A-2C are replicate profiles, meaning that the data files from which they are derived represent data acquired for identical samples under identical experimental conditions and settings. Nevertheless, because of the inherent variability associated with chromatographic separation, both the major and minor features of sample profile 220 are temporally offset with respect to the corresponding features of reference profile 210.

FIG. 2B depicts the partially aligned profiles 210 and 220 after application of the pre-alignment step 120 to the respective data files. Notably, the major features of the profiles (marked by an oval) are aligned, while minor features of the profiles (examples of which are marked by a box) remain misaligned. The partially aligned data files are used as input to the full alignment step 230. The fully aligned profiles are shown in FIG. 2C. It may be discerned that both the major features (marked by the oval) and minor features (marked by the box) are well-aligned.

Figure 3:
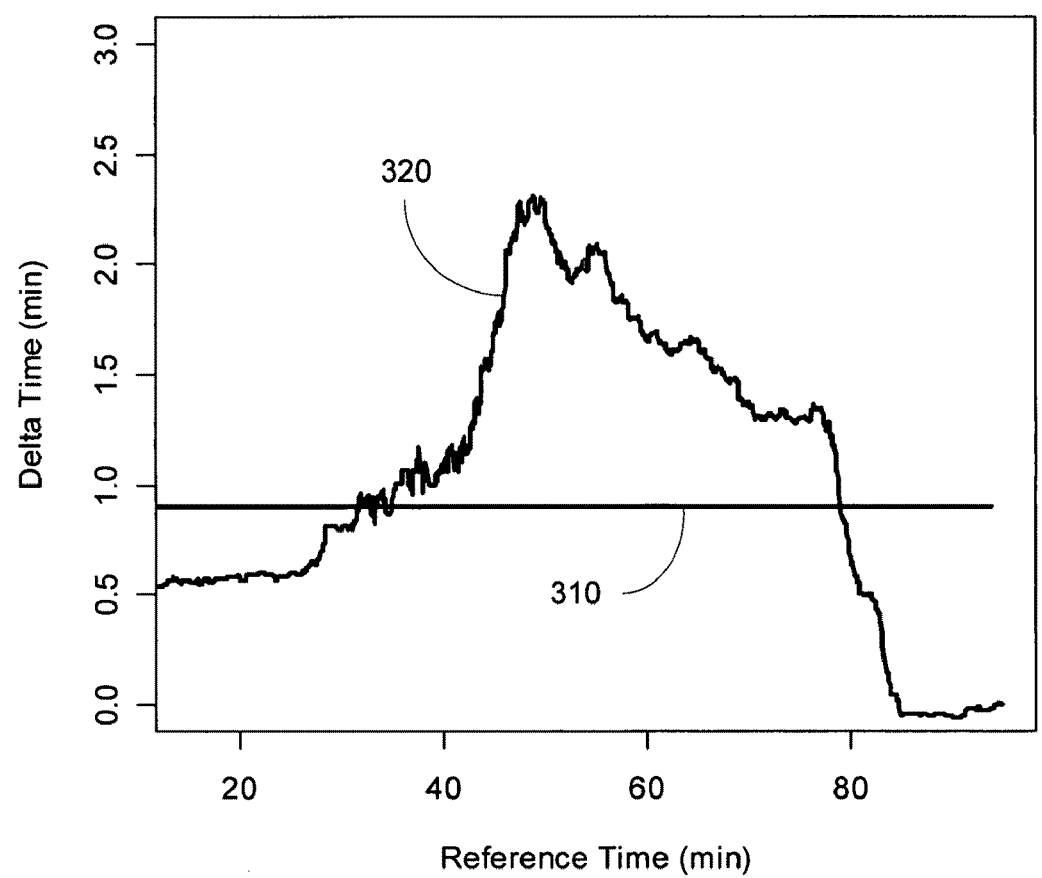
FIG. 3 depicts the time warping function for the aligned chromatograms.

FIG. 3 depicts the time warping function for the alignment of the chromatographic profiles depicted in FIGS. 2A-2C. The horizontal line 310 represents the time shift obtained from the pre-alignment step 120, and the complex curve 320 represents the final time-warping function obtained from the full alignment step 130. At approximately 38 minutes, the warping function oscillates about the time shift obtained in the pre-alignment step. This example demonstrates that the pre-alignment step is an accurate representation of alignment at the elution times of the major ion species.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A mass spectrometric analysis method that is performed on a computer, comprising steps of:
    acquiring mass spectrometry data as a plurality of data files, each data file being representative of the mass-to-charge ratios and intensities of ions detected during analytical scans;
    pre-aligning the data files using base peak information derived therefrom;
    constructing a correlation matrix from full MS scan data in the pre-aligned data files; and
    determining an optimal path through the correlation matrix; and
    temporally aligning the data files by identifying aligned scan numbers in the data files based on the optimal path.

2. The method of claim 1, wherein the step of pre-aligning data files includes steps of:
    constructing two-dimensional chromatographic profiles using base peak retention times and intensities; and
    determining a time shift that maximizes the dot product of the two-dimensional chromatographic profiles.

3. The method of claim 2, wherein the step of determining the time shift includes calculating a correlation between the two-dimensional chromatographic profiles.

4. The method of claim 3, wherein the correlation is calculated by taking the inverse Fourier transform of the product of the Fourier transforms of the two-dimensional chromatographic profiles.

5. The method of claim 1, wherein the step of constructing the correlation matrix includes calculating correlation values for only those elements that fall within a time window determined from the pre-alignment step.

6. The method of claim 1, wherein the step of determining the optimal path includes determining a path that maximizes a sum of correlation values that lie on the path.

7. The method of claim 6, wherein the step of determining the optimal path includes the step of calculating a path matrix D, each element Dij of path matrix D corresponding to an optimal path leading to Dij.

8. The method of claim 1, wherein the data files include a reference data file and at least first and second sample data files, and wherein both the first and the second sample data files are temporally aligned to the reference data file.

9. The method of claim 1, further comprising a step of applying a filter to the data files prior to performing the pre-aligning step.

10. The method of claim 1, wherein the step of determining the optimal path includes calculating a path score representative of the quality of the alignment.

11. The method of claim 1, further comprising the steps of examining chromatographic profiles corresponding to the data files to identify differences.

* * * * *